(12) United States Patent
Passi

(10) Patent No.: US 10,492,765 B2
(45) Date of Patent: Dec. 3, 2019

(54) SYSTEM AND METHOD FOR CONTROLLING AN ULTRASOUND TRANSMISSION/RECEPTION APPARATUS

(71) Applicant: STMICROELECTRONICS S.R.L., Agrate Brianza (MB) (IT)

(72) Inventor: Stefano Passi, Pavia (IT)

(73) Assignee: STMICROELECTRONICS S.R.L., Agrate Brianza (MB) (IT)

(*) Notice: Subject to any disclaimer, the term of this patent is extended or adjusted under 35 U.S.C. 154(b) by 625 days.

(21) Appl. No.: 15/145,132

(22) Filed: May 3, 2016

(65) Prior Publication Data
US 2017/0065258 A1   Mar. 9, 2017

(30) Foreign Application Priority Data

Sep. 9, 2015   (IT) .................. 102015000050094

(51) Int. Cl.
| | |
|---|---|
| *A61B 8/00* | (2006.01) |
| *A61B 8/14* | (2006.01) |
| *B06B 1/02* | (2006.01) |
| *G01S 15/89* | (2006.01) |
| *G10K 11/34* | (2006.01) |

(52) U.S. Cl.
CPC ............ *A61B 8/54* (2013.01); *A61B 8/14* (2013.01); *A61B 8/4483* (2013.01); *B06B 1/0207* (2013.01); *G01S 15/8915* (2013.01); *G10K 11/346* (2013.01); *B06B 2201/20* (2013.01)

(58) Field of Classification Search
CPC ........... A61B 8/4483; A61B 8/14; A61B 8/54; B06B 1/0207; B06B 2201/20; G01S 15/8915; G10K 11/346
See application file for complete search history.

(56) References Cited

U.S. PATENT DOCUMENTS

| | | |
|---|---|---|
| 5,142,649 A | 8/1992 | O'Donnell |
| 5,186,175 A | 2/1993 | Hirama |
| 8,648,629 B2 | 2/2014 | Rossi |
| 8,710,874 B2 | 4/2014 | Rossi |
| 8,749,099 B2 | 6/2014 | Rossi |
| 8,947,150 B2 | 2/2015 | Ghisu |
| 2003/0048698 A1 | 3/2003 | Barnes |

(Continued)

*Primary Examiner* — Amanda Lauritzen Moher
*Assistant Examiner* — Chao Sheng
(74) *Attorney, Agent, or Firm* — Slater Matsil, LLP

(57) ABSTRACT

A control system for an ultrasound transmission/reception apparatus with a plurality of acoustic transducers for transmitting and receiving ultrasound signals may include driving device operatively coupled to the acoustic transducers and a control unit. The control unit may cyclically control the acoustic transducers in a transmission state for transmitting ultrasound signals, and in a reception state for receiving echoes of the transmitted ultrasound signals. The control unit may include an input stage which receives an external timing signal, and a processing stage which detects a first edge of the timing signal to determine the start time of a transmission phase during which the acoustic transducers are controlled in the transmission state, and a second edge of the timing signal to determine the stop time of a reception phase during which the acoustic transducers are controlled in the reception state.

16 Claims, 5 Drawing Sheets

(56) References Cited

U.S. PATENT DOCUMENTS

| | | | |
|---|---|---|---|
| 2010/0087737 A1* | 4/2010 | Iwama | A61B 8/00 600/447 |
| 2010/0174194 A1* | 7/2010 | Chiang | A61B 8/4488 600/447 |
| 2011/0245677 A1* | 10/2011 | Sato | A61B 8/08 600/447 |
| 2012/0268189 A1 | 10/2012 | Rossi | |
| 2013/0265855 A1 | 10/2013 | Ghisu | |

* cited by examiner

SYSTEM AND METHOD FOR CONTROLLING AN ULTRASOUND TRANSMISSION/RECEPTION APPARATUS

TECHNICAL FIELD

The present invention relates to a system and a method for controlling an ultrasound transmission/reception apparatus, in particular for ultrasound imaging applications.

BACKGROUND

Ultrasound is used for imaging applications, in the clinical field for ultrasonographic investigations, for example. An ultrasound transmission/reception apparatus generally includes a plurality of acoustic transducers (e.g., example piezoelectric or microphone transducers) which are appropriately controlled to generate ultrasound pulses, and for receiving the echo generated by the ultrasounds after they have impinged on a target of interest (for example, a portion of the human body, in the case of ultrasonographic investigations).

In particular, beamforming techniques may be used for driving the acoustic transducers. During transmission, the acoustic transducers are driven with suitable relative time delays to focus the ultrasound beams generated by each acoustic transducer onto the target of interest, thus creating suitable constructive or destructive interference patterns (which is generally known and not described in detail herein). During reception, the time delays are taken into consideration while processing the signals received by a receiver device of the ultrasound transmission/reception apparatus.

As illustrated schematically in FIG. 1, an ultrasound transmission/reception apparatus 101 having a plurality of channels (six in the illustrated example, although other numbers may be used), illustratively includes a set of acoustic transducers 102. For example, the transducers 102 may be piezoelectric transducers arranged in an array, such as a linear array or a matrix array (usually one for each channel), suitably driven for generating respective ultrasound beams during a transmission phase, and further for receiving the echo of the generated ultrasounds during a subsequent reception phase which is temporally distinct from the transmission phase.

The apparatus 101 further illustratively includes a driving device 103 coupled to the acoustic transducers 102 for supplying suitable electrical driving signals and controlling an operating state of the acoustic transducers 102. A receiver device 104 is coupled to the acoustic transducers 102 during the reception phase for managing reception of the ultrasound echoes received on the various channels.

In particular, the driving device 103 also includes a control unit 105 designed or configured to suitably time the phases of transmission and reception and to manage biasing of the acoustic transducers 102 during the same transmission and reception phases. A plurality of pulse-generation units 106 are each coupled to a respective channel and are managed by the control unit 105 for supplying respective driving signals $S_d$, typically high-voltage impulse signals, to the corresponding acoustic transducers 102. The driving signals $S_d$ have suitable waveforms and are appropriately delayed in time with respect to one another (for example, with a delay increasing from a first channel with the shortest delay (e.g., a zero delay) to a second channel with the highest delay) to cause generation of ultrasound beams directed towards a common target B. The increase in delay is represented schematically by the arrow in FIG. 1. The delays may be linearly decreasing, and it may also be possible to have different delay configurations, e.g., with the longest delay on a central channel and delays that decrease towards the outer channels.

The receiver device 104 in turn includes a plurality of receiving units 107 which are selectively coupled (e.g., through switching elements not shown in the present example) to the acoustic transducers 102 during reception of the ultrasound echoes for processing (e.g., via filtering and amplification operations), and potentially converting from analog to digital to enable subsequent processing thereof. The detected ultrasound signals are received with different delays due to the different distances covered starting from the common target B. The receiver device 104 further illustratively includes a reconstruction unit 108 that is coupled to the receiving units 107 and is designed or configured to suitably compensate the delays and synchronize the ultrasound signals received by the various channels to enable subsequent imaging, e.g., ultrasonographic imaging.

Conveniently, the driving device 103 may be an integrated device, for example in the form of an integrated circuit chip with a package. More particularly, the driving device 103 and the receiver device 104 may be integrated within a same chip. The ultrasound transmission/reception apparatus 101 is further coupled to an external supervision unit 109, e.g., a management unit of a sonographer in which the ultrasound transmission/reception apparatus 101 is used, which manages operation thereof according to the ultrasonographic investigations that are to be carried out.

The external supervision unit 109 (which may include, for example, a microprocessor, a microcontroller, an FPGA or similar processing unit) is distinct from the control unit 105 of the driving device 103 (each has respective processing capability), and co-operates with the same control unit 105 (and with the reception device 104) for implementing a control system 100. The control system 100 controls operation of the ultrasound transmission and reception by the ultrasound transmission/reception apparatus 101.

In particular, the control unit 105 of the driving device 103 is configured to control the acoustic transducers 102 in the following different operating states, according to the operations to be performed. In an inactive state (i.e., a "clamp" or "setup" state), the acoustic transducers 102 are inactive (e.g., the acoustic transducers 102 are connected to a ground reference voltage). The inactive state may correspond to a wait phase prior to a subsequent phase of transmission or reception of ultrasounds, as described in greater detail below.

In a transmission state, the acoustic transducers 102 are biased by the high-voltage driving signals $S_d$, with appropriate waveforms, for generation of the ultrasound beams. In a reception state, the acoustic transducers 102 are configured to receive the echo generated by the ultrasound beams during the previous transmission phase.

Typically, after the transmission phase the acoustic transducers 102 are set in the inactive state for a pre-set time (which generally has the function of eliminating residual vibrations or oscillations on the acoustic transducers 102). After this, the same acoustic transducers 102 are set in the reception state. Following the reception phase, the acoustic transducers 102 are again set in the inactive state, waiting for the subsequent transmission phase (the inactive phase may be used for operations of setup of the ultrasound transmission/reception apparatus 101). The foregoing operating states are repeated in a periodic, cyclic way during operation of the ultrasound transmission/reception apparatus 101.

While the timing of the remaining state transitions may be managed internally, the ultrasound transmission/reception apparatus 101 receives certain information externally, in particular from an external supervision unit 109. First, an indication of the start instant START is provided, i.e., when the transmission phase is started and the previous inactive phase of the acoustic transducers 102 is terminated. Second, an indication of the stop instant STOP is provided, i.e., when the reception phase is terminated and the acoustic transducers 102 shift again to the inactive phase.

The external supervision unit 109 makes these determinations based upon acoustic environment and of the operating requirements, which are linked to the nature of the sonographic investigation, for example. This is done at the start of each cycle of the transmission phase and for the time interval during which the acoustic transducers 102 are to receive the ultrasound echoes. For example, the time of reception of the ultrasound echoes may be linked to the depth from the surface at which the target B of the sonographic investigation is located.

The present Applicant has realized that the mode of externally supplying the start START and stop STOP indications to the transmission/reception apparatus 101 may be significant. In particular, typical approaches contemplate that the START and STOP indications are supplied via respective commands received through a serial communication interface, for example an SPI or I2C interface, or similar data-communication interface.

The present Applicant has also realized that use of a similar communication interface requires, however, a considerable time interval for reading and interpreting the commands, which is intrinsic to the communication protocol used. This time interval has to be considered and correctly evaluated by the external supervision unit 109, also considering the fact that, in an ultrasound system, the correct calculation of the times of transmission/reception/inactivity is important for proper operation.

Furthermore, the activity of the serial clock required for operation of the communication protocol may disturb the operations of reception of the ultrasound echoes. In particular, this may result in errors in reception. In this regard, it should be noted that the electrical signals associated with ultrasound echoes typically have a small amplitude. Thus, in general, use of this mode of transmission of the command indications may be susceptible to errors and malfunctioning.

Other approaches send appropriate digital command signals from the external supervision unit 109 to the ultrasound transmission/reception apparatus 101, each of which encodes a respective operating phase of transmission, reception, and inactivity. The present Applicant has realized, however, that this approach entails the risk of the digital command signals not being correctly received and/or correctly interpreted. Moreover, even if the digital command signals are synchronized correctly in the transmission phase by the external supervision unit 109, they may reach the driving device 103 of the ultrasound transmission/reception apparatus 101 with delays different from those set forth in the design stage, for example on account of different paths of propagation of the same signals. The lack of synchronization of the digital command signals may result in errors and potentially be harmful in some operating situations.

Further approaches encode the sole indication of start of the transmission phase by the level of a digital control signal. For example, this may be switched from a first value to a second value for a pre-set number of clock pulses. However, the present Applicant has realized that this approach may also be subject to risks of errors and malfunctioning, in particular due to possible erroneous readings of the level of the digital control signal (e.g., due to glitches or spurious pulses that may be present), or to a failure in reading the same digital control signal (e.g., as a result of an incorrect synchronization of the clock).

SUMMARY

An object is to help overcome the problems of the above-described approaches, and in particular to provide an approach which may be more effective and safe for providing respective indications of starts and stops of the transmission and reception phases to an ultrasound transmission/reception apparatus.

According to an example embodiment, a control system is for an ultrasound transmission/reception apparatus having a plurality of acoustic transducers for transmitting and receiving ultrasounds. The system may include a driving device operatively coupled to the acoustic transducers and having a control unit configured to cyclically control the acoustic transducers in a transmission state to transmit ultrasounds, and in a reception state to receive the echoes of the ultrasounds transmitted. The control unit may include an input stage configured to externally receive a timing signal from outside the driving device, and a processing stage. The processing stage may be configured to detect a first edge of the timing signal at which it determines the start of a transmission phase, during which the acoustic transducers are controlled in the transmission state. The processing stage may further detect a second edge of the timing signal at which it determines when to stop a reception phase in which the acoustic transducers are controlled in the reception state.

A related control method for an ultrasound transmission/reception apparatus is also provided.

BRIEF DESCRIPTION OF THE DRAWINGS

Example embodiments will now be described, purely by way of non-limiting example, with reference to the attached drawings, in which.

BRIEF DESCRIPTION OF THE DRAWINGS

Figure 1:
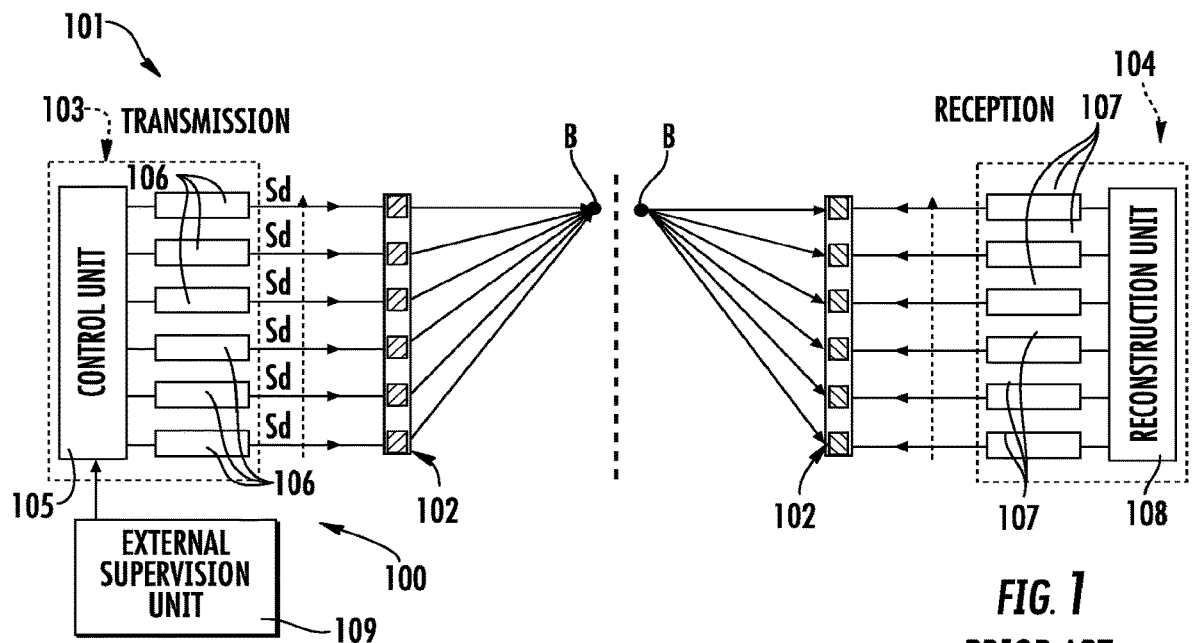
FIG. 1 is a schematic block diagram of an ultrasound transmission/reception apparatus and of a corresponding control system in accordance with the prior art.
Figure 2:
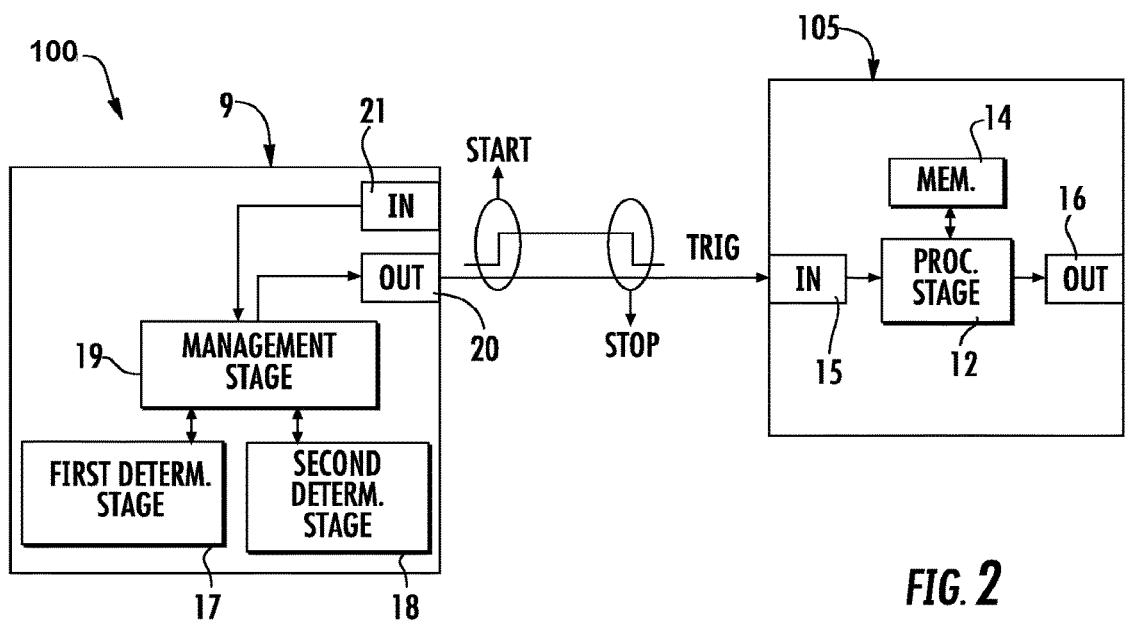
FIG. 2 is a schematic block diagram of a control system for an ultrasound transmission/reception apparatus according to an example embodiment.

Turning now to FIG. 2, a first example embodiment of a control system 100 is now described for an ultrasound transmission/reception apparatus 101, which may have a structure similar to that shown in FIG. 1 and described above. As such, the transmission/reception apparatus 101 is not reproduced in the subsequent drawings and will not be described again in detail below.

According to one aspect, the above-described command indications of start START, and stop STOP, are supplied to the control unit 105 of the driving device 103 of the ultrasound transmission/reception apparatus 101 by the external supervision unit 109, via a single timing signal or trigger signal Trig. For example, this may be a square-wave signal.

In particular, a first edge (e.g., the rising edge) of the trigger signal Trig determines the start instant or time START of the transmission phase. A second edge (e.g., the falling edge) of the trigger signal Trig determines the stop instant STOP of the phase of reception of ultrasounds by the acoustic transducers 102. Furthermore, the periodic repetition of the waveform (e.g., square-wave) of the trigger signal Trig determines the cyclic succession of the phases of ultrasound transmission and reception.

More particularly, the control unit 105 illustratively includes a processing stage 12, which may be configured to implement a finite-state machine that evolves as a function of an internal clock, for example. Furthermore, a memory 14 may include a RAM non-volatile memory and/or one or more registers, operatively coupled to the processing stage 12. An input stage 15 is illustratively coupled to the processing stage 12 and configured to receive signals from the external supervision unit 109. An output stage 16 is coupled to the processing stage 12 and configured to transmit signals to the pulse-generation units 106 of the driving device 103 (see FIG. 1).

The external supervision unit 109 illustratively includes a first determination stage 17 configured to determine the instant of start, i.e., the rising edge, of the trigger signal Trig. The determination may be based upon the operations, e.g., ultrasonographic investigations, to be made and of the corresponding acoustic environment, for example. A second determination stage 18 is configured to determine the temporal duration of the trigger signal Trig, and thus the falling edge of the same trigger signal Trig. A management stage 19 is coupled to the first and second determination stages 17, 18 and is configured to generate the trigger signal Trig as a function of the duration and of the corresponding starting instant supplied by the first and second determination stages 17, 18. A respective output stage 20 is coupled to the management stage 19 and is configured to transmit signals to the control unit 105 of the driving device 103. Furthermore, a respective input stage 21 is coupled to the management stage 19 and is configured for signal reception.

Figure 3:
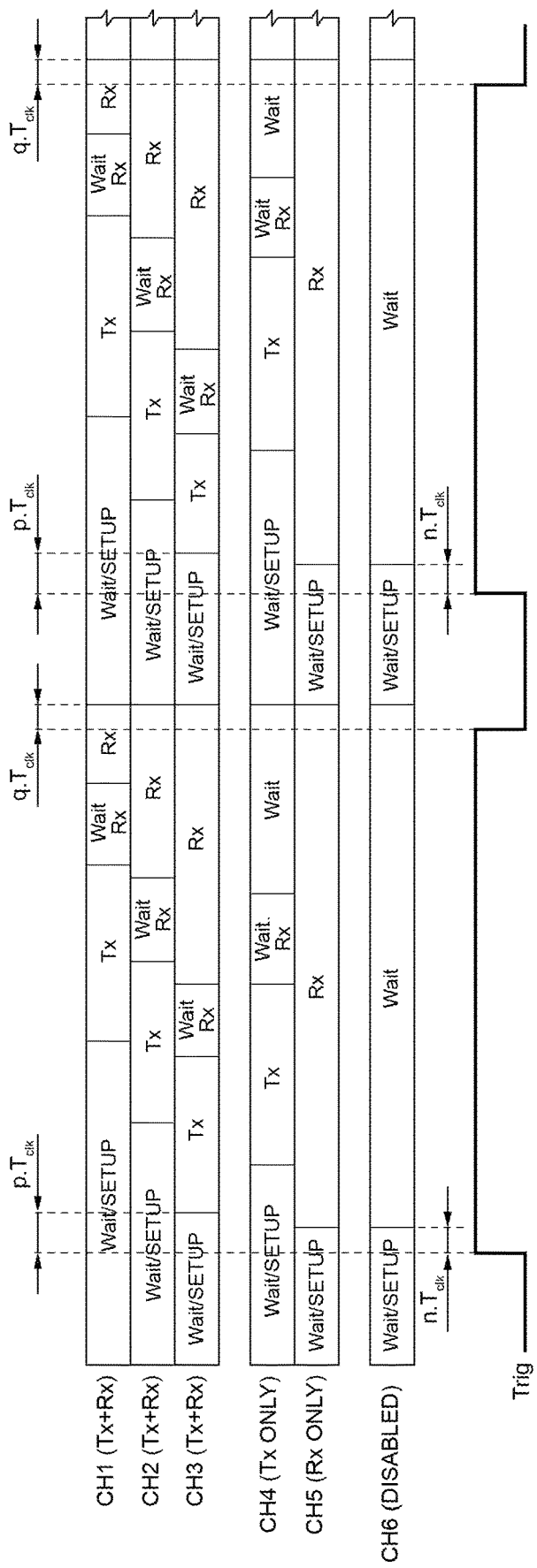
FIG. 3 is a timing diagram illustrating operating states and control signals associated with the control system of FIG. 2.

Operation of the control system 100 of the ultrasound transmission/reception apparatus 101 is now described with particular reference to FIG. 3, which illustrates one example case in which six channels (CH1-CH6) are present and coupled to the acoustic transducers 102 (which are also six in number in this example). Three channels CH1-CH3 are configured to transmit and receive ultrasounds, channel CH4 is configured only to transmit ultrasounds, channel CH5 is configured only to receive the ultrasound echoes, and channel CH6 is configured in a disabled state. It should be noted that each channel in the ultrasound transmission/reception apparatus 101 may be configured individually, with reference to each operating cycle, for transmission only, for reception only, transmission/reception, or else be disabled.

It is assumed that initially all the channels are in the inactive state, waiting to carry out a new phase of ultrasound transmission having variable delays with respect to an common initial instant. These delays may be dependent on the beamforming algorithm used, for example. In this phase, configuration of the ultrasound transmission/reception apparatus 101 may be performed. For example, this may include configuration of the parameters of the waveforms that are to be generated by the pulse-generation units 106, which may be conveniently stored in the memory 14.

The control unit 105 of the driving device 103 of the ultrasound transmission/reception apparatus 101 receives from the external supervision unit 109 the trigger signal Trig, and the corresponding processing stage 12 identifies (e.g., with an edge detector) the first edge (i.e., the rising edge) thereof. The rising edge is associated with the start instant START of the ultrasound transmission phase. In particular, after the start instant START, the various channels begin the respective transmission phase (if they are enabled for transmission) in synchronization with the start instant, in a temporally staggered way, with the respective pre-set time delays, and they then shift into the reception state.

In the present example, moreover, as an exception to the transmission/reception operation generally used, after a first pre-set time interval (e.g., equal to a first number n of cycles of the internal clock $n \cdot T_{clk}$, where $T_{clk}$ is the clock period), the channel CH5 goes into the reception state, and the channel CH6 goes into the inactive wait state. Alternatively, a pre-set delay may be used after the end of the number n of clock cycles. In particular, after a pre-set second number p of clock cycles (with n<p), the channel CH3, which is pre-set to have a shorter or minimum delay time in the beamforming algorithm, goes into the transmission state.

It should be noted that the first and second pre-set numbers of clock cycles n, p depend upon the intrinsic delays pre-set and stored in the control unit 5. These may potentially be equal to a single clock period $T_{clk}$.

Next, with pre-set delays that depend upon the beamforming algorithm implemented, the other channels which are enabled for transmission/reception go into the transmission state (in this case the channel CH2, and then the channel CH1, which has the maximum delay). Further, in this embodiment, the channel CH4, which operates in the sole pulse-transmission state, also shifts into the transmission state after a pre-set delay subsequent to the second number p of clock cycles.

In general, with respect to the same starting instant START, which represents the common synchronization instant, the start instant $T_i$ of the transmission operations of each channel $CH_i$ (enabled in transmission and reception) may be expressed as:

$$T_i = p \cdot T_{clk} + \text{delay}_i$$

where $\text{delay}_i$ is the pre-set delay associated with each channel (which, in the present example, is equal to 0 for the channel CH3). It should also be noted that different profiles of the delay time between the various channels may be used, for example a parabolic profile, with maximum delay at a central channel and delays decreasing towards the outer channels.

Next, the transmission state of each channel lasts for a pre-set time interval (which may be the same for one or more of the channels, for example, although they may be different), after which each channel shifts to the inactive state waiting for the next reception phase (if enabled). Also, the duration of the wait state is pre-set (e.g., it is stored in the memory 14 of the control unit 105) and is, for example, the same for one or more of the channels.

From the wait state, each enabled channel then shifts to the reception state, the end of which is subsequently determined commonly for all the channels by the second edge. In the present example, this is the falling edge of the trigger signal Trig, which is also determined by the processing stage 12 of the control unit 105.

In particular, each channel terminates the reception phase, passing from the reception state again into the inactive state, after a third number q of clock cycles from the falling edge of the trigger signal Trig. In the present example, q<n<p, with q possibly having a minimum duration that is, in a limit case, equal to a single clock period $T_{clk}$. The entire transmission and reception cycle is repeated cyclically in a similar manner upon arrival of the next first edge (e.g., the rising edge) of the trigger signal Trig, as shown in the FIG. 3.

It should be noted that the frequency of the trigger signal Trig consequently determines the pulse-repetition frequency (PRF). The duty cycle of the same trigger signal Trig determines the ratio of the interval of reception with respect to the inactive wait interval of the next transmission phase. These intervals are the only intervals of a duration that is not defined internally by the control device 106, but is established from outside based on the command indications received from the external supervisor device 109.

Figure 4A:
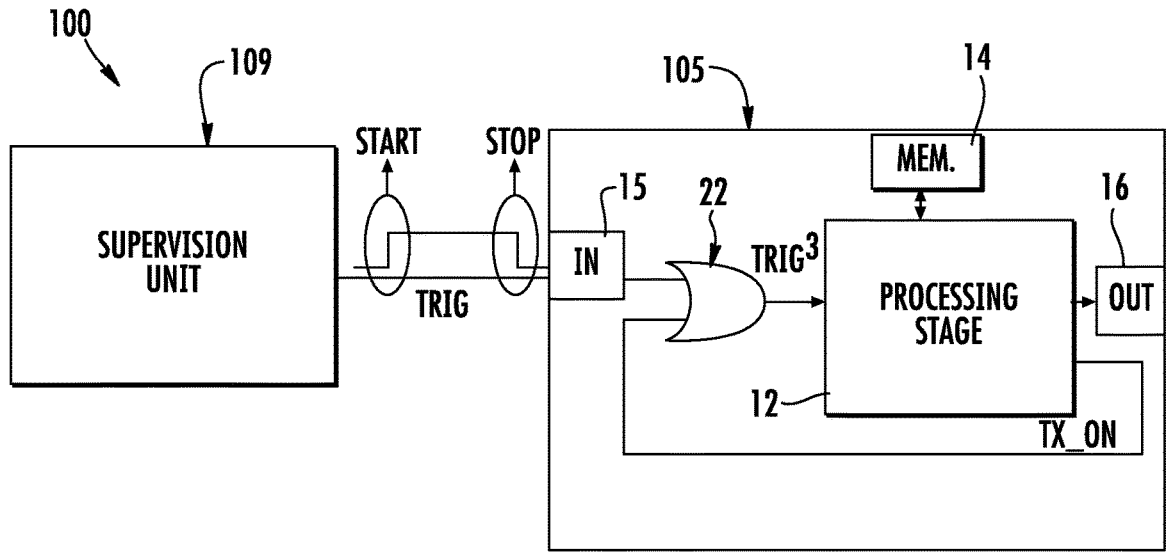
FIG. 4A is a schematic block diagram of a control system for an ultrasound transmission/reception apparatus in accordance with another example embodiment.
Figure 5A:
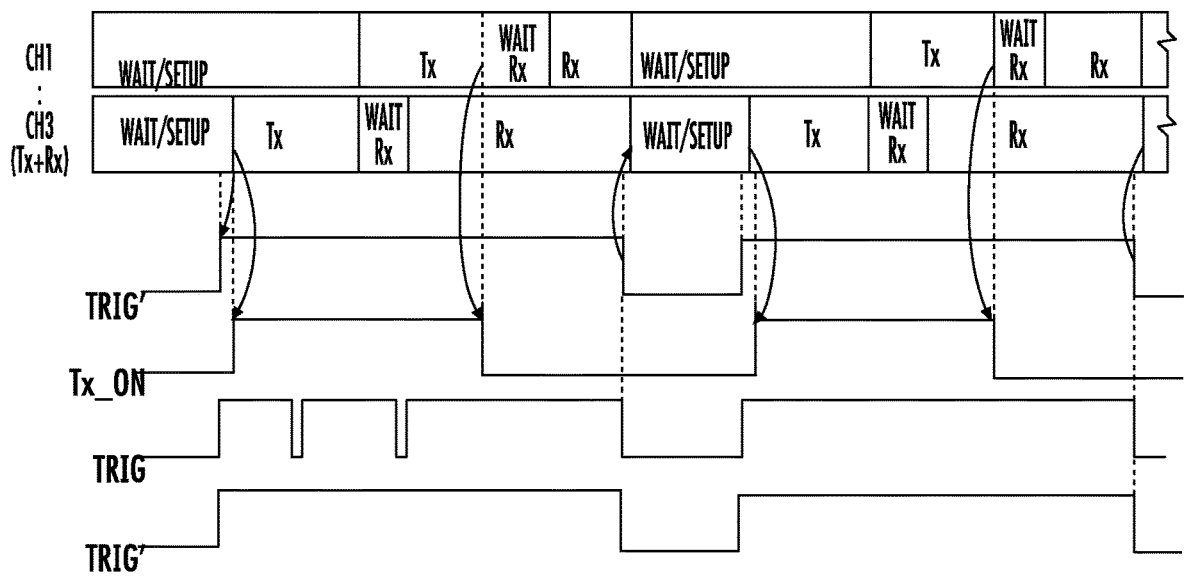
FIG. 5a is a timing diagram illustrating operating states and control signals which may be associated with the control system of FIG. 4B or 4B.

With reference to FIGS. 4a and 5a, another embodiment is now described which allows for carrying out a safety check on the trigger signal Trig received from the external supervision unit 109. It should be noted that in FIG. 4a, for clarity of illustration, the external supervision unit 109 is not shown in detail (the supervision unit may be similar to that shown in FIG. 2, for example).

The present Applicant has realized that the trigger signal Trig may be affected by noise or glitches, which may sometimes jeopardize proper execution of the operations performed by the ultrasound transmission/reception apparatus 101. A further aspect of the present approach thus helps ensure that the second edge (e.g., the falling edge) of the trigger signal Trig (which is to determine the end of the reception phase and the start of the inactive phase to wait for the next ultrasound transmission) effectively occurs during a phase of reception of the ultrasound echoes, and not during a phase of ultrasound transmission, for example, as a result of the disturbance that may be present on the trigger signal Trig.

In this embodiment, the control unit 105 is configured to generate a timing signal Tx_ON indicating the active presence of a transmission phase on at least one channel. In FIG. 5a for clarity of illustration, only the timing plots for the channel CH3, with the shortest time delay, and the channel CH1, with the longest time delay in transmission, are shown. The timing signal Tx_ON switches to the high state at the start of the first phase of transmission by the channel CH3, and then switches to the low state at the end of the last phase of transmission by the channel CH1. In other words, the high state of the timing signal Tx_ON is indicative of the presence of an active transmission phase by any one of the channels of the driving device 103.

The timing signal Tx_ON is in this case logically combined with the trigger signal Trig to generate a corrected trigger signal Trig'. This operation of logic combination enables, as highlighted in FIG. 5a (see in particular the bottom plots), removal of potential disturbances present in the trigger signal Trig during the transmission phase. In other words, it makes it possible to neglect any falling edges of the same trigger signal Trig that occur within the transmission phase. In this case, it is the falling edge of the corrected trigger signal Trig' which corresponds to the effective falling edge of the trigger signal Trig that determines the next end of the reception phase.

In the embodiment illustrated in FIG. 4a, the control unit 105 therefore includes a logic-combination stage 22, which in the illustrated example includes an OR logic gate that receives from the input stage 15 the trigger signal Trig and combines it logically with the timing signal Tx_ON generated by the processing stage 12 within the same control unit 105. This generates the corrected trigger signal Trig', which is used by the processing stage 12 to determine the end of the reception phase.

Figure 4B:
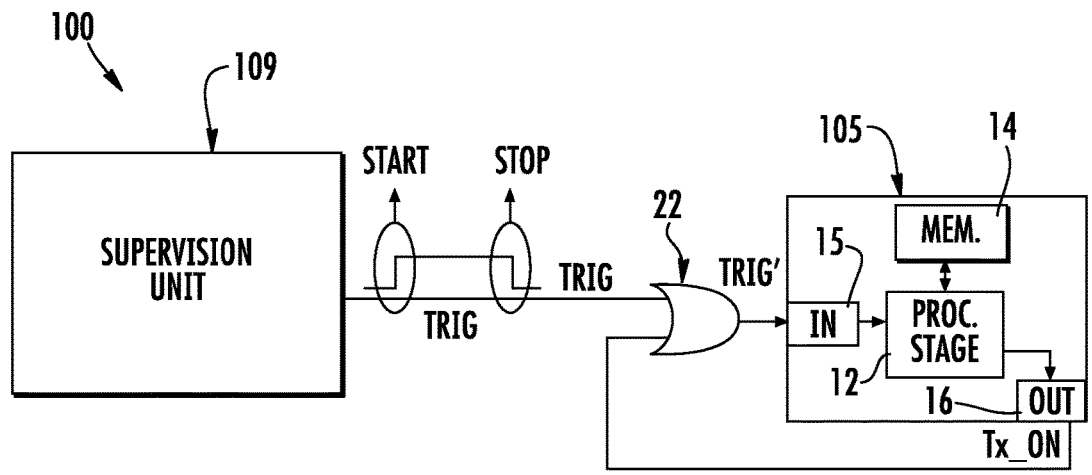
FIG. 4B is a block diagram of a variant of the control system of FIG. 4A.

As illustrated in FIG. 4b (where, for clarity of illustration, the external supervision unit 109 is again not presented in full detail), in another example embodiment, the operation of logic combination is carried out outside the control unit 105 of the driving device 103. This is done by a logic-combination stage 22 which receives the timing signal Tx_ON from the same control unit 105 and the trigger signal Trig from the external supervision unit 109, and then supplies the corrected trigger signal Trig' at the input of the control unit 105. The logic-combination stage 22 may be included within the same external supervision unit 109, which in this case receives as feedback the timing signal Tx_ON from the control unit 105.

Generally speaking, greater safety may be afforded by the approach illustrated in FIG. 4a, where the risk that the corrected trigger signal Trig' might also be affected by noise and by disturbance is minimized. This is a possibility that may instead arise in the case where the corrected trigger signal Trig' is generated outside the control unit 105.

Figure 5B:
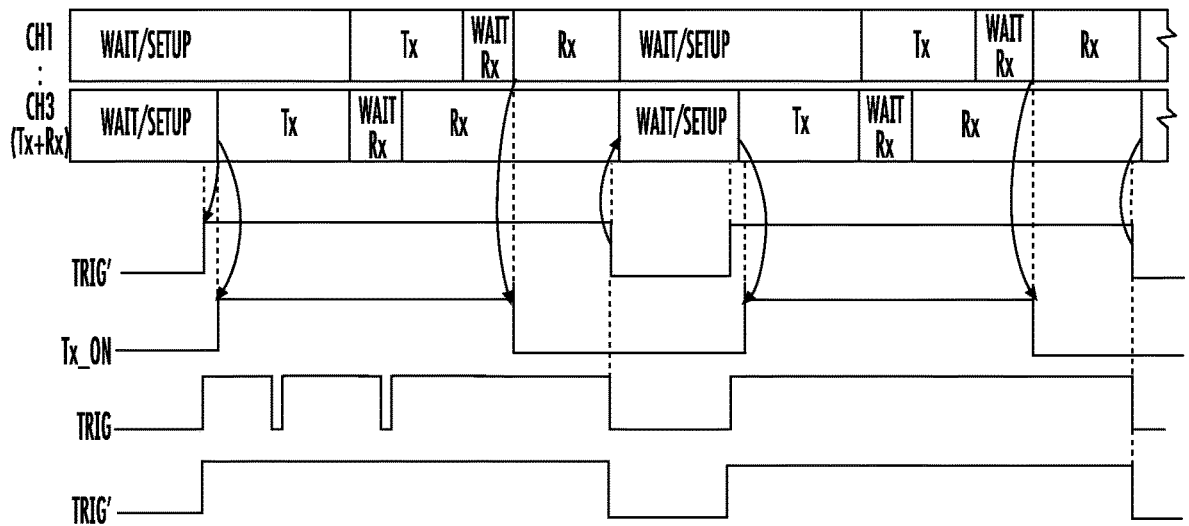
FIG. 5b is a timing diagram illustrating operating states and control signals which may be associated with the control system of FIG. 4B or 4B.

Still another embodiment is shown in FIG. 5b (which again represents the timing plots only of the channels CH1 and CH3). This may instead have the timing signal Tx_ON with a high value also during the inactive phases that follow the transmission phases. In this case, switching to the low state of the timing signal Tx_ON thus occurs at the end of the inactive phase (which follows the transmission phase) of the last channel CH1 (having the longest delay in the formation of the ultrasound beams in the beamforming algorithm). The above embodiment may offer a still greater safety, since it helps reduce possible disturbances of the trigger signal Trig that may arise during the inactive phase, in addition to the disturbance potentially present in the transmission phase).

Figure 6:
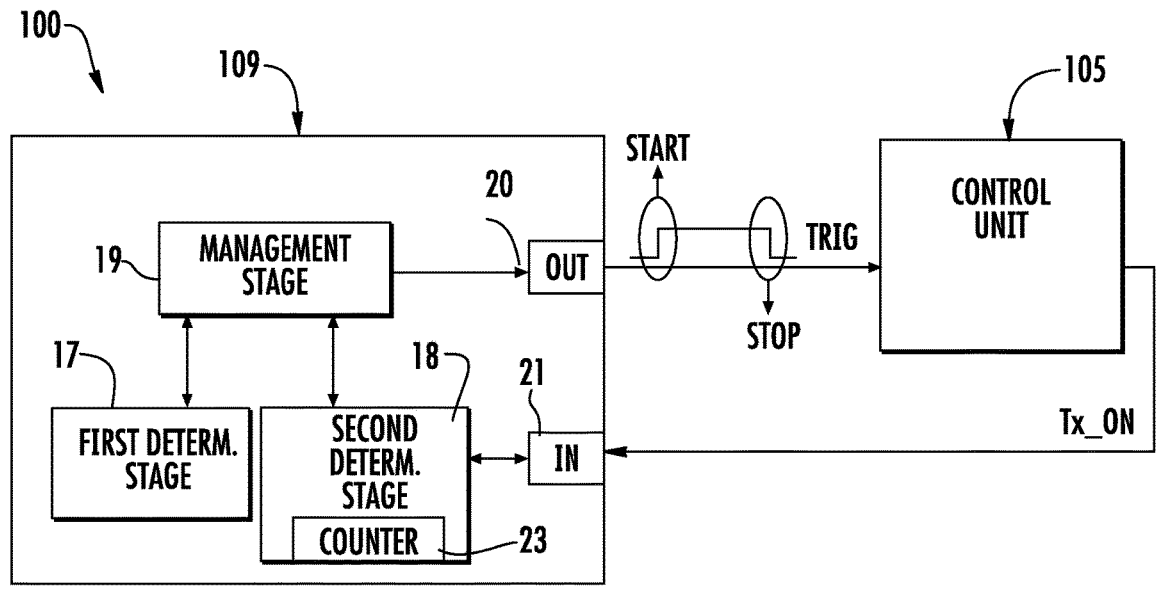
FIG. 6 is a schematic block diagram of a control system for an ultrasound transmission/reception apparatus in accordance with another example embodiment.
Figure 7:
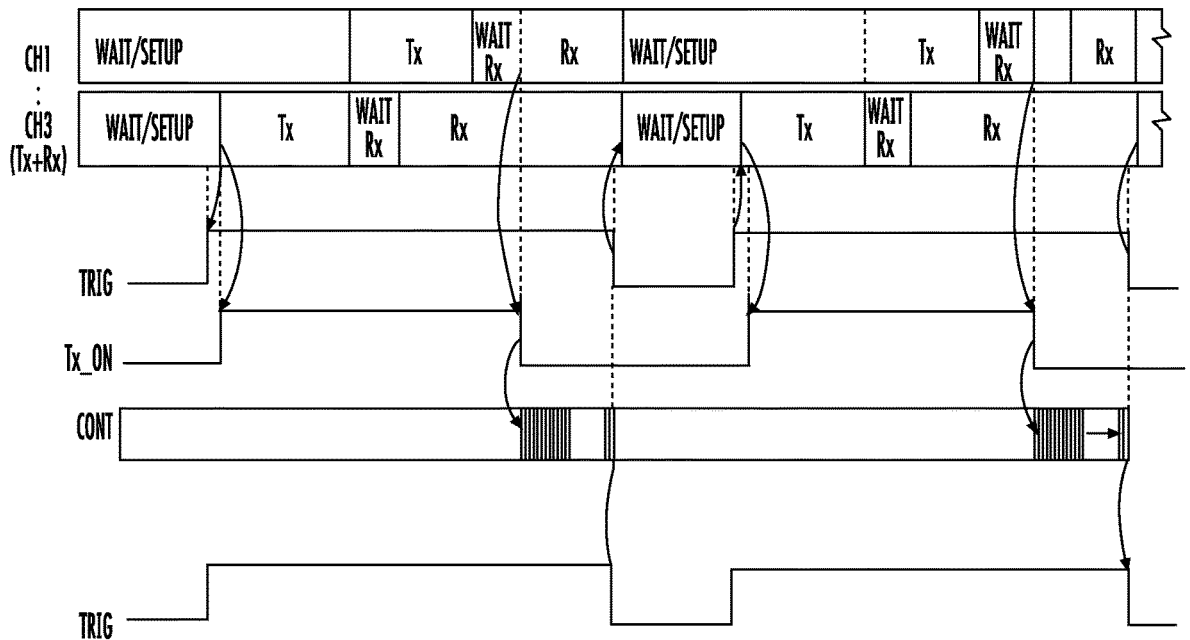
FIG. 7 is timing diagram illustrating operating states and control signals which may be associated with the control system of FIG. 6.

Another embodiment is now described with reference to FIG. 6 (where, for clarity of illustration, the control unit 105 is again not shown in full detail) and to FIG. 7 (where, for clarity of illustration, the timing plots of just the channels CH1 and CH3 are shown). In this embodiment, the timing signal Tx_ON generated internally by the control unit 105 is supplied as feedback to the external supervision unit 109, contributing to the formation of the trigger signal Trig.

In particular, the second determination stage 18 of the external supervision unit 109 is in this case configured to receive the timing signal Tx_ON and includes an internal counter 23. The counter 23 is started at the falling edge of the same timing signal Tx_ON and performs a count equal to the desired duration of the reception phase (which in turn depends upon the operations to be carried out, e.g., on the parameters of the ultrasonographic investigations).

In this case, the total duration of the trigger signal Trig, to which the corresponding falling edge is associated, is thus determined automatically as a function of the timing signal Tx_ON received as feedback from the control unit 105 of the driving device 103. This may be done as the sum of the duration of the transmission phase (determined by the same control unit 105 on the basis of the effective transmission operations carried out on the various channels and communicated to the external supervision unit 109 via the duration of the high state of the timing signal TX_ON), and the desired duration of the reception phase.

In particular, the management stage 19 generates the trigger signal with rising edge determined by the first determination stage 17 (as described previously). The falling edge is determined by the end of the count made by the counter 23 starting from the end of the timing signal Tx_ON.

This embodiment has an advantage of simplifying the operations of calculation performed by the external supervision unit 109 for determining the trigger signal Trig, in light of the known difficulties that may be present in determination, via calculations, of the duration of the transmission phase. These may involve consideration of several parameters corresponding to the waveforms used in the ultrasound transmission by the various channels, for example.

The advantages of proposed approaches will be appreciated from the preceding description. In any event, it is again emphasized that use of a single trigger signal Trig for determining (via detection of the corresponding rising and falling edges) the instants of start of the transmission phase and stop of the reception phase enables considerable simplification of the operations performed in the ultrasound transmission/reception apparatus 101.

In particular, controlling timing of the transmission and reception operations is faster, simpler, and also proves to be safer, in that it is immune from the problems that confront prior approaches. These include a possibility of errors in decoding the received command signals, or the possibility for the clock of serial protocols to interfere with the same command signals.

Advantageously, a disturbance, glitches, crosstalk, and interference of various kind, or system errors do not interfere with proper execution of the transmission and reception operations in accordance with the example embodiments described above. In addition, the use of the timing signal Tx_ON for implementing a control of the validity of the trigger signal Trig received from outside the ultrasound transmission/reception apparatus 101 enables further increase in safety of the operations carried out.

The same timing signal Tx_ON, received as feedback, may further enable simplification of the operations performed by the external supervision unit 109 for generation of the trigger signal Trig. This further simplifies the control system 100 of the ultrasound transmission/reception apparatus 101, and further increases the rate of execution of the operations. It may be further emphasized that control of repetition of the pulses may be advantageously obtained from the periodic evolution of a square-wave trigger signal Trig, for example.

Various modifications and variations may be made to what has been described and illustrated herein, without thereby departing from the scope of the embodiments, as defined in the attached claims. In particular, it is again emphasized that the ultrasound transmission/reception apparatus 101 may be advantageously used in a wide range of applications and not only in the medical field. For example, it may be used in applications of structural investigation or of analysis of materials via application of ultrasounds.

Furthermore, the number of acoustic transducers 102, and consequently the number of channels used in the ultrasound transmission/reception apparatus 101, may be different in different embodiments. For example, ultrasound transmission/reception apparatuses 101 may be obtained having sixteen or more channels. Moreover, the arrangement of the acoustic transducers 102 may be in the form of a linear array or a matrix.

The invention claimed is:

1. A control system for an ultrasound apparatus comprising a plurality of acoustic transducers for transmitting and receiving ultrasound signals, the control system comprising:
a driving device coupled to the acoustic transducers and comprising a control unit configured to cyclically control the acoustic transducers in a transmission state to transmit ultrasound signals, and in a reception state to receive echoes of the transmitted ultrasound signals, wherein the acoustic transducers are associated with respective channels;
said control unit comprising:
an input stage configured to receive from outside said driving device a timing signal; and
a processing stage configured to detect a first edge of the timing signal to determine a start time of a transmission phase of the acoustic transducers during which the acoustic transducers are controlled in the transmission state, and to detect a second edge of the timing signal to determine a stop time of a reception phase during which the acoustic transducers are controlled in the reception state, wherein said control unit is configured to:
control the channels in the transmission state in a temporally staggered manner with different time delays starting from the start instant following detection of the first edge of the timing signal;
end the reception state of the channels based upon the stop instant following detection of the second edge of the timing signal; and
generate a transmission-feedback signal indicating a duration of the transmission phase; and
a logic-combination stage configured to logically combine the transmission-feedback signal and the timing signal for preventing the second edge of the timing signal from occurring during said transmission phase.

2. The system of claim 1, wherein said control unit, following detection of the second edge of the timing signal, is configured to control the channels in an inactive state and wait for a subsequent phase of transmission of ultrasound signals, and is further configured to control the channels in the transmission state for a set duration, in an inactive state for the set duration following the transmission state, and in the reception state following the inactive state.

3. The system of claim 1, wherein said transmission-feedback signal comprises a logic signal having a first value indicating the transmission phase and a second value indicating an absence of the transmission phase; and wherein said logic-combination stage comprises an OR logic gate configured to receive the transmission-feedback signal and the timing signal and generate a corrected timing signal for said processing stage.

4. The system of claim 1, further comprising an external supervision unit configured to generate and send the timing signal to said control unit; and wherein said external supervision unit is further configured to receive as a feedback from said control unit the transmission-feedback signal and to generate the timing signal as a function of the transmission-feedback signal.

5. The system of claim 1, wherein said logic-combination stage is internal to said control unit.

6. The system of claim 1 further comprising an external supervision unit configured to generate and send the timing signal to said control unit.

7. The system of claim 6 wherein said external supervision unit comprises:
- a counter;
- a first determination stage configured to determine the first edge of the timing signal; and
- a second determination stage configured to determine the second edge of the timing signal at end of a count by said counter of a desired reception interval starting from the end of the transmission-feedback signal.

8. An ultrasound apparatus comprising:
a plurality of acoustic transducers for transmitting and receiving ultrasound signals; and
a control system comprising
a driving device coupled to the acoustic transducers and comprising a control unit configured to cyclically control the acoustic transducers in a transmission state to transmit ultrasound signals, and in a reception state to receive echoes of the transmitted ultrasound signals;
said control unit comprising
an input stage configured to receive from outside said driving device a timing signal, and
a processing stage configured to detect a first edge of the timing signal to determine a start time of a transmission phase of the acoustic transducers during which the acoustic transducers are controlled in the transmission state, and to detect a second edge of the timing signal to determine a stop time of a reception phase during which the acoustic transducers are controlled in the reception state, wherein said control unit is further configured to generate a transmission-feedback signal indicating a duration of the transmission phase; and wherein said control system further comprises a logic-combination stage configured to logically combine the transmission-feedback signal and the timing signal for preventing the second edge of the timing signal from occurring during said transmission phase.

9. The ultrasound apparatus of claim 8, wherein said transmission-feedback signal comprises a logic signal having a first value indicating the transmission phase and a second value indicating an absence of the transmission phase; and wherein said logic-combination stage comprises an OR logic gate configured to receive the transmission-feedback signal and the timing signal and generate a corrected timing signal for said processing stage.

10. The ultrasound apparatus of claim 8 further comprising an external supervision unit configured to generate and send the timing signal to said control unit.

11. The ultrasound apparatus of claim 8 wherein said acoustic transducers are associated with respective channels; and wherein said control unit, following detection of the first edge of the timing signal, is configured to control the channels in the transmission state in a temporally staggered manner with different time delays starting from the start instant; and wherein, following detection of the second edge of the timing signal, said control unit is configured to end the reception state of the channels based upon the stop instant.

12. The ultrasound apparatus of claim 11 wherein said control unit, following detection of the second edge of the timing signal, is configured to control the channels in an inactive state and wait for a subsequent phase of transmission of ultrasound signals, and is further configured to control the channels in the transmission state for a set duration, in an inactive state for the set duration following the transmission state, and in the reception state following the inactive state.

13. A control method for an ultrasound apparatus including a plurality of acoustic transducers for transmitting and receiving ultrasound signals, the method comprising:
cyclically controlling the acoustic transducers in a transmission state for transmitting ultrasound signals, and in a reception state for receiving the echoes of the transmitted ultrasound signals by
receiving from outside the ultrasound apparatus a timing signal and detecting a first edge of the timing signal to determine a start time of a transmission phase during which the acoustic transducers are controlled in the transmission state, and detecting a second edge of the timing signal to determine a stop time of a reception phase during which the acoustic transducers are controlled in the reception state;
generating, inside the ultrasound apparatus, a transmission-feedback signal indicative of the duration of the transmission phase; and
logically combining the transmission-feedback signal and the timing signal to prevent the second edge of the timing signal from occurring during the transmission phase.

14. The method of claim 13, wherein the transmission-feedback signal comprises a logic signal having a first value indicating the transmission phase and a second value indicating an absence of the transmission phase; and wherein the logic combination comprises combining via an OR logic gate the transmission-feedback signal and the timing signal and to generate a corrected timing signal.

15. The method of claim 13, further comprising generating the timing signal as a function of the transmission-feedback signal.

16. The method of claim 13, wherein generating the timing signal comprises determining the second edge of the timing signal at an end of counting of a desired reception interval starting from the end of the transmission-feedback signal.

* * * * *